US008689602B2

(12) United States Patent
Rossiter

(10) Patent No.: US 8,689,602 B2
(45) Date of Patent: Apr. 8, 2014

(54) TESTING DETECTORS

(75) Inventor: William Rossiter, Welham Green (GB)

(73) Assignee: Sata Limited, Hertfordshire (GB)

( * ) Notice: Subject to any disclaimer, the term of this patent is extended or adjusted under 35 U.S.C. 154(b) by 460 days.

(21) Appl. No.: 11/663,904

(22) PCT Filed: Sep. 27, 2005

(86) PCT No.: PCT/GB2005/003711
§ 371 (c)(1),
(2), (4) Date: Aug. 14, 2008

(87) PCT Pub. No.: WO2006/035216
PCT Pub. Date: Apr. 6, 2006

(65) Prior Publication Data
US 2009/0078065 A1 Mar. 26, 2009

(30) Foreign Application Priority Data
Sep. 27, 2004 (GB) .................................. 0421435.9

(51) Int. Cl.
*G01N 33/06* (2006.01)

(52) U.S. Cl.
USPC .......................................................... 73/1.06

(58) Field of Classification Search
None
See application file for complete search history.

(56) References Cited

U.S. PATENT DOCUMENTS

| | | | | |
|---|---|---|---|---|
| 4,464,575 | A * | 8/1984 | Cholin et al. | 250/554 |
| 4,590,789 | A * | 5/1986 | Kunze | 73/1.06 |
| 5,668,302 | A * | 9/1997 | Finbow et al. | 73/23.2 |
| 6,282,940 | B1 * | 9/2001 | Hung et al. | 73/1.06 |
| 2002/0047782 | A1 * | 4/2002 | Schneider et al. | 340/577 |
| 2004/0050137 | A1 * | 3/2004 | Hoppenworth | 73/1.06 |
| 2005/0204799 | A1 * | 9/2005 | Koch | 73/1.06 |
| 2007/0062249 | A1 * | 3/2007 | Forrest | 73/1.06 |

FOREIGN PATENT DOCUMENTS

| | | | |
|---|---|---|---|
| GB | 2176600 | 12/1986 | |
| JP | 1-72695 | 5/1989 | G08B 17/10 |

OTHER PUBLICATIONS

Japanese Search Report (with English Translation) (dated Nov. 2, 2010—4 pages).

* cited by examiner

*Primary Examiner* — Robert R Raevis
(74) *Attorney, Agent, or Firm* — Renner, Kenner, Greive, Bobak, Taylor & Weber

(57) ABSTRACT

A hazard detector assembly for attachment to a surface within a protected zone comprises a detector unit and a test stimulus generator unit.

8 Claims, 2 Drawing Sheets

TESTING DETECTORS

Fire detectors including but not limited to smoke, heat, CO or combination detectors need to be tested for function. Tests are commonly specified by national and international standards amongst other. Most such tests are designed to ensure that the detector is capable of receiving a fire stimulus of the type the detector is designed to detect, from the protected area and into the sensing area of the detector.

Currently the most common method of complying with these recommendations and requirements is for an individual to visit each detector in turn and, using a special test device carried on the person, introduce such a stimulus. Specialised tools are common within the fire detection 'maintenance industry'.

Smoke detectors are commonly tested by means of an aerosol canister that produces synthetic smoke particles perhaps in conjunction with a specialist dispensing device.

Heat detectors might be tested by means of a wide range of devices ranging from the distinctly 'amateur', including such things as cigarette lighters or hair dryers, to more professional devices.

Carbon monoxide detectors are newer to the market and considerably less widespread than the other types. Where they are tested it might be by means of a canister of pressurised carbon monoxide or by a range of other surrogate products.

All of these products and activities have the common theme that they involve a person visiting each detector with a test device to simulate the physical stimulus that the detector is designed to detect. While the introduction of the physical stimulus is vital to a correct and proper test the necessity of both visiting and accessing each and every detector (usually required at least on an annual basis for every detector) adds to the time and cost of service and maintenance of the system. Many would like to improve and possibly automate the process.

Modern 'intelligent' fire detection products are capable of reporting, to some extent, on the condition of the detector by confirming the analogue value at the detector. This might be achieved by interrogation of the control panel or by a hand held device carried on the person in much the same way as the test equipment described above is carried on the person. Some of the hand held devices communicate with the detector by means of infra-red. All of these types of test have the disadvantage that that are purely 'electronic tests' and do not involve introduction of physical stimuli (actual or surrogate smoke, heat, CO, etc) as the standards recommend and/or require. As such, although they 'have their place' they are inadequate to fulfil the need of a genuine functional test.

Separately, it has been proposed to incorporate a facility, within the detector, for producing a test. These proposals mean incorporating such a device/feature at the point of manufacture of the detector itself by the detector manufacturer. This is not integration of a test source with the detector but physical integration within the detector.

More recently it has been proposed in EP-A-1325299 (Tormaxx) that certain and various advantages exist by placing the test source in permanent position adjacent to the detector. The advantages of this proposal are several fold. They include the fact that the person does not have to physically access detectors individually (perhaps with a pole for detectors at height). A further advantage is that time is saved and disruption is lessened. In addition, and importantly, such an in situ test device can be supplied or fitted separately and perhaps at a later date to the core fire system itself.

Although the Tormaxx proposal refers to battery power it is not considered currently viable for batteries to provide sufficient power to meet the needs of this type of product at an appropriate cost and efficiency. The reality of the proposal is, therefore, that it requires separate wiring either for device power, control or both. A separate disadvantage is that a principal proposal within the Tormaxx patent is for the tester to be permanently fixed adjacent to the detector. This leads to a possible concern relating to a potential conflict with design and installation codes and standards for fire detectors that state that detectors cannot be mounted immediately adjacent to other items (for reasons of airflow). In the British standard, for example, the requirement is that detectors should be mounted at least twice the distance from a ceiling projection as is the depth of that ceiling projection. The further that the adjacent device has to be from the detector the greater potential for a less efficient test. A separate disadvantage is that objections may be raised on aesthetic grounds.

In the context of the present invention there are at least three connotations of the word 'remote'. The first is through the control and indicating equipment or, as it is often known, 'the panel' that controls the fire detection system. The second, usually through this same panel, is for control or interrogation from a remote centre such as a monitoring station (which may, in reality, be several hundred miles distant). The third, in a more local application is in the form of a small controller carried on the person and which might communicate with the detector via various methods including but not limited to wires or cables, infra-red or radio. Indeed small hand-held remote controllers are not uncommon within fire detection systems and are usually used as programming tools or loop testers. Some go so far as to claim that they 'test' the detector but are limited to electronic tests of the detector that do not involve physical stimuli such as the introduction or control of smoke, heat or acceptable surrogate stimuli. As such they do not meet the requirements of codes and standards now commonly known as 'functional testing'.

DESCRIPTION AND ADVANTAGES OF THIS INVENTION

In the present invention a test device, if not incorporated into a detector base at the time of manufacture of that base, can be fitted, between the base of a detector and the ceiling (or between the base and the detector itself). The result is an 'in line' test device that is capable of producing actual stimuli to test the detector under test and can do so by a wide number of methods including, for example those described in EP-A-1325299. This in-line test device can be controlled by and/or powered by a number of alternative methods.

In order that the present invention be more readily understood, embodiments thereof will now be described by way of example with reference to the accompanying drawings, in which:—

In all the figures, the same reference numerals are used to represent the same parts.

Figure 1:
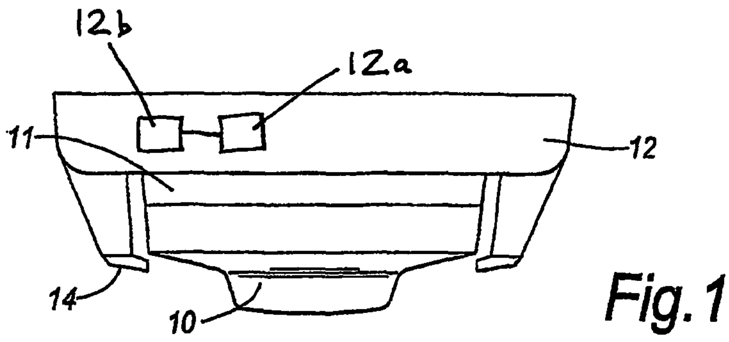
FIG. 1 shows a side view of a first embodiment of the present invention.
Figure 2:
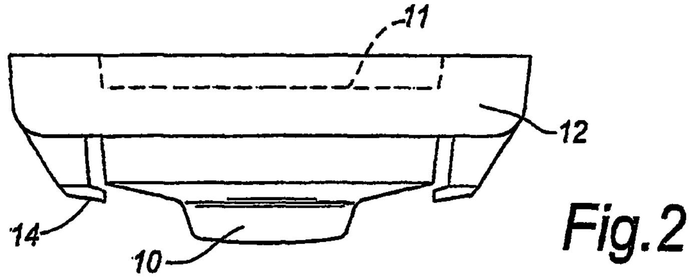
FIG. 2 shows a side view of a modification to the embodiment shown in FIG. 1.
Figure 3:
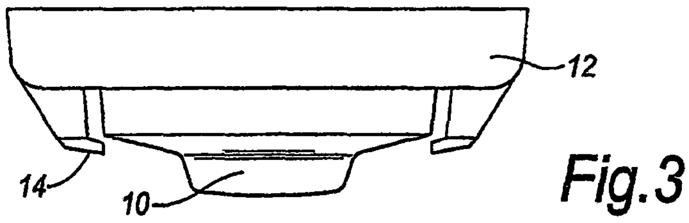
FIG. 3 shows a side view of a further modification to the embodiment shown in FIG. 1.
Figure 4:
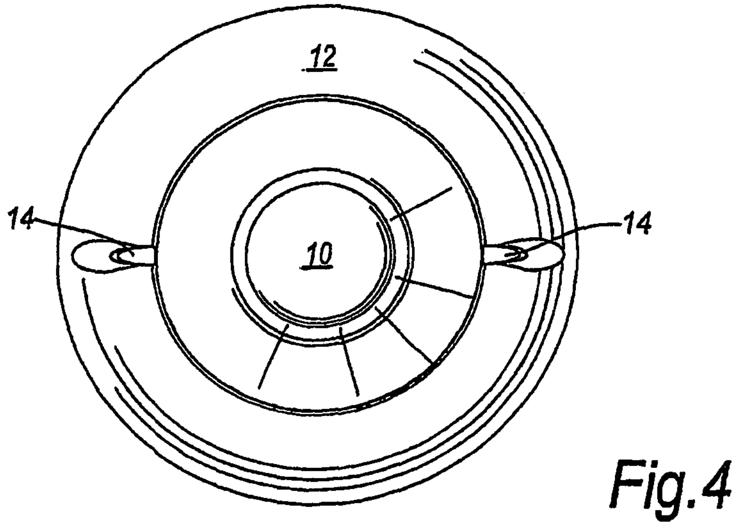
FIG. 4 shows a plan view of the embodiment shown in FIG. 1.

As shown in FIG. 1, a complete detector/tester assembly comprises a detector 10, a detector base 11 attached to a suitable surface and to which the detector is attached, and a tester unit 12. The tester unit 12 has a generator 12*b* arranged to generate one or more stimuli eg smoke, heat and/or CO from a source of stimulus material 12*a*. The stimulus generated is directed on to the exterior of the detector 10 by means of one or more delivery outlets 14. As shown in FIGS. 1 to 3, the delivery outlets comprise a duct which extends generally perpendicular to the plane of the ceiling on which the assembly is mounted. The duct may end in a nozzle or outlet portion which is arranged to direct the stimulus towards the detector 10.

The tester unit 12 is mounted so as to be co-axial with the detector base 11 and detector 10 i.e. in a line normal to the surface to which the assembly is attached. Preferably, the unit 12 is symmetrical and slightly larger in diameter than the detector 10. It is, however, possible to have a tester unit of substantially the same cross-sectional shape and size as the detector and then have one or more delivery tubes extend from the tester unit so that the free end of the tube or tubes is located in the vicinity of the detector.

In FIG. 1, the tester unit 12 is fixed to a suitable surface such as a ceiling and then the usual base 11 is attached to the tester unit.

In FIG. 2, the tester unit is fixed between the base 11 and the detector 10 either by being attached to the base 11 or simply by being attached to the supporting surface. In either case, electrical connections to the base 11 are required so that the normal wiring to the base 11 need not be disturbed.

In FIG. 3, the tester unit is designed to replace the base 11 and the detector is attached to the tester unit.

In order to deliver the stimulus to the detector 10, it may be necessary to fit the tester unit 12 with a fan or some other fluid moving device (not shown).

Figure 5:
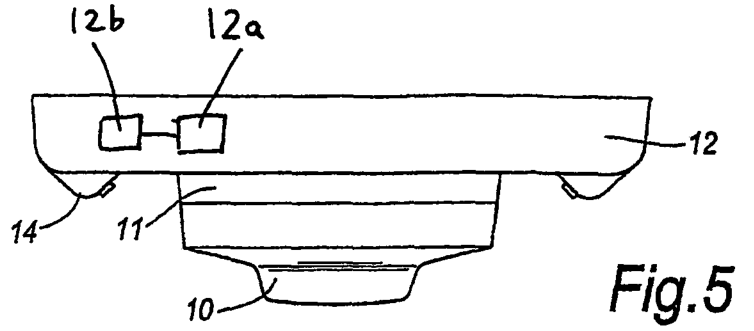
FIG. 5 shows a side view of a second embodiment of the present invention.
Figure 6:
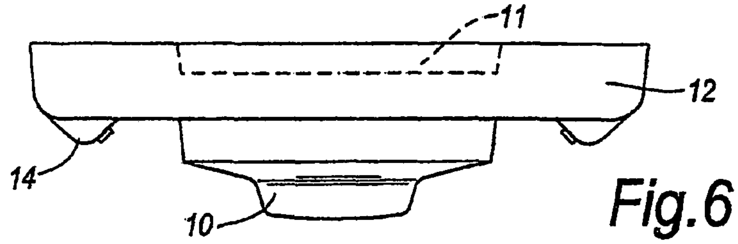
FIG. 6 shows a side view of a modification to the embodiment shown in FIG. 5.
Figure 7:
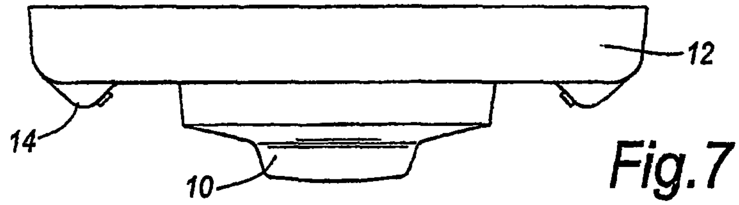
FIG. 7 shows a side view of a further modification to the embodiment shown in FIG. 5.
Figure 8:
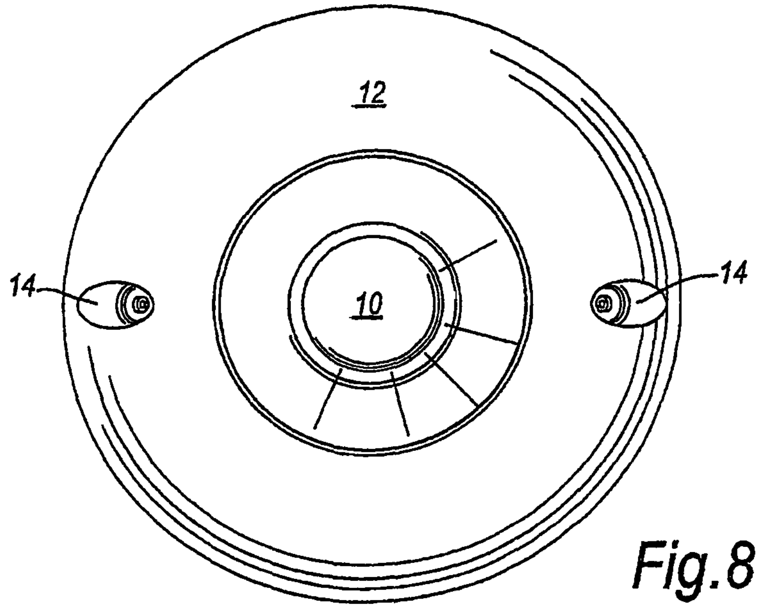
FIG. 8 shows a plan view of the embodiment shown in FIG. 5.

The embodiment shown in FIG. 5 as well as the modifications shown in FIGS. 6 and 7 are similar to the first embodiment except that the delivery outlets are different. In the embodiment shown in FIG. 5 there are no ducts as such but the tester unit 12 is fitted with protuberances which have an inwardly angled face fitted with the outlet nozzle.

Although two delivery outlets 14 are shown in the drawings, this number and the dispersion of the outlets can be changed. Also, when the tester unit 12 is arranged to generate a number of different stimuli, different stimuli can be fed to different outlets or the same stimulus can be fed to all outlets.

With these constructions in mind, the following are features of an in-line tester/detector assembly according to the present invention.

Actual Test a. The test includes physical stimuli of the type that the detector is designed to detect. This might include, but not be limited to, appropriate particulate for a smoke detector, carbon monoxide gas for a CO detector, heat for a heat detector or a combination of appropriate stimuli for multi criteria detectors b. The test stimuli is generated outside the detector, from within the protected area, such that the stimulus is obliged to pass from the protected area through any vents, openings or other barriers to the sensing area of the detector (thereby helping to verify free passage). Note that this is different to a stimulus being generated from within the detector itself and which does not test access to the sensing chamber from outside.

Positioning c. Detectors may be situated in difficult to access places such as, but not limited to, ceiling spaces, floor voids, ducts, mountings at height or behind aesthetic features such as ceiling grids or mesh sheets, or behind cable trays can be tested easily. Detectors in easily accessible positions can be tested in the same manner.

d. The test device is integrated with but not within the detector.

e. In a favoured design, the test device becomes a third component of the detector where the first is the detector and the second the detector base (except in the instance that a detector and base are one unit in which case the test device is the second device). The tester can, if required, be supplied and installed independently from the core fire detection system itself. As such the test device can be manufactured separately from the detector and base and a standardised design used with different fire detectors. Flexibility and wider scope can also be retained in the commercial process of quotation, supply and installation. In addition, should a decision be taken to install such an 'in situ' test device then this can be done either at the same time that the rest of the system is installed or retrospectively. Such a concept enables currently installed systems to have these devices fitted.

f. In one embodiment, the test device may be incorporated within the detector base. This has some cost advantages over the concept of a separate device. Conversely it has some limitations. One limitation might occur in the event that a base incorporates, for example, smoke test facilities and becomes 'redundant' in the event that the smoke detector is one day exchanged for a heat or other type of fire detector later in the life of the system. Base testers would also be suitable only for a particular make or range of detectors in the same way that bases and detectors are not now interchangeable between different types, makes or ranges.

g. An in-line device can be designed to be fitted between the detector and base with the additional advantage of benefiting from the bayonet type fitting that is commonplace with most detectors (in this instance on both sides) and being able to be fitted or removed easily (in much the same way as can be the detector itself). As such it can be 'retro fitted' very easily as well as be fitted at the time of installation. This makes it appealing to a very wide market indeed.

h. The 'in line' design ('e' or 'f' above) permits the physical test media to be 'delivered', if required, to the detector from any angle or number of angles up to 360 degrees around the detector if required. This can have advantages since some detectors are more sensitive to stimuli from one direction than another but exactly which orientation is best is rarely known by the person installing an adjacent test device. Similarly, the person installing does not, in this way, have to account for the direction of airflow within the environment.

i. The in line device might have a diameter greater than the diameter of the detector itself, thereby enabling test media to be directed or blown backward from any angle or number of angles up to 360 degrees around the detector if required at the detector such as to improve the ability of the test media to enter the sensing area j. The 'in line' design ('e' or 'f' above) is more aesthetically pleasing than separate testers, adjacent to the detector.

k. The 'in line' design ('e' or 'f' above) enables, if required, power, control, or both, to be integrated from within the existing power and control of the fire system, minimising wiring complications and/or benefiting from control synergies.

l. In the instance of an 'in line' device and particularly one that fits between detector and base using, for example, the double bayonet approach, additional wiring or installation activities are kept to the absolute minimum (or negated completely), thereby saving on both materials and, importantly, labour.

Control m. The test stimulus for an in line tester may need to be controlled and limited in its output, duration and/or timing. The reasons for this might include, for example, a need to conserve power or, separately, a need not to contaminate the environment/protected area.

n. Control might need to influence the amount of test stimulus, the type of test stimulus or the profile of test stimulus (particularly important from multi sensor type detectors or detectors designed to respond to a particular algorithm of stimuli) or a combination of the foregoing. By way of example the test device might be instructed in a given situation to produce a slowly increasing of concentration of particulate, a limited quantity of CO, a time limited amount of heat or a combination of the above. It might also include a clearing procedure by which the stimuli is then removed from the sensor under test. Under certain circumstances such control might also enable a check of the sensitivity of the detector and/or the degree of free access to the sensing chamber or area.

o. Through a variable control mechanism, the type, characteristics or profile of the test introduced to the detector may be varied on a subsequent occasion. This need might arise, for example, because the detection characteristics have been changed. Either because the detector has been replaced with a different detector or, in the case of a multi sensor, the configuration changed.

p. The in line tester may need to be individually operated for each detector or, if desired, controlled such that a group of such devices be operated to activate more than one detector at a time (each detector activated being confirmed as such by either reviewing the illuminated LED or by confirmation from the fire control system itself)

q. Control for the test device might be pre-set within the test device itself or initiated, adjusted, varied and/or stopped remotely. In this use of the word 'remotely' brings with it a number of alternatives mentioned earlier. It may for example mean a portable control unit carried by a person initiating a test on site. Such personnel currently visit each detector and perform the test but are now obliged to bring the test media to the detector. In the instance where this does not involve ladders and/or scaffolding it usually involves a special pole with a piece of test equipment at the top. Both methods involve more labour and disruption (even should access enable them to be performed at all) than a remote control unit that communicates with the tester from a distance by using, for example, infrared, bluetooth or other technology. There are a wide number of advantages of the test being controlled by a person on the site and these include but are not limited to the fact that they physically inspect and observe the detector and its surroundings at the same time as performing the test. Such inspection is also recommended and/or required by codes and standards. Control of the test device in this manner would not require protocol co-ordination with the panel and detector that is, for the most part, necessary in the following alternative.

r. Alternative control can be provided by or through the panel that controls the detector under test. One of the advantages of this is that the test could be conducted without having to 'visit' each of the detectors individually. It is technically possible for tests to be conducted in this way without even visiting the site itself since tests can be initiated and controlled operated over a telephone or other link. This is similar to the manner in which, today, it is technically feasible to isolate a detector remotely or to reconfigure it from being a smoke detector to a heat detector.

Power s. The test device requires power (typically a few mA). While it is possible for power to be provided by batteries it is also possible for the device to be designed such that power is drawn from the same (usually low voltage) source as provides power to the detector. In the instance that battery power is to be used, the life of the batteries may be a concern and safeguards would need to be in place to ensure that the batteries are not exhausted when they need to be relied on. In the instance that the test device draws its power from the detector supply, and should it require instantaneous power greater than that available from that provided to the detector, a charge storage capacitor may be built into the test device which can gradually charge over a longer period of time in order to deliver more power in the test situation

The invention claimed is:

1. A hazard detector assembly for attachment to a surface within a protected zone, said hazard detector assembly comprising a detector unit and a test stimulus generator unit for testing said detector unit, said stimulus generator unit comprising a body receiving a source of stimulus material and a generator device for generating a stimulus from the source of the stimulus material, the body being provided with means for attaching said detector unit to be tested and with a means for directing the generated stimulus from outside the detector unit towards the detector unit when attached, wherein the body of the stimulus generator unit further comprises means for fixedly mounting the stimulus generator unit to said surface within said protected zone, said stimulus generator unit is positioned between said detector unit and said surface, and wherein the stimulus generator unit is adapted to generate a stimulus for testing the detector unit while being fixed to the surface.

2. A hazard detector assembly according to claim 1 wherein the body is provided with means for attaching the stimulus generator unit to a base member.

3. A hazard detector assembly according to claim 1 wherein the attachment means for attaching said detector unit is on a major surface opposite a further surface by which the stimulus generator unit is attached to a base member or a surface.

4. A hazard detector assembly according to claim 1, wherein said detector unit and said test stimulus generator unit are connected together in a line normal to the surface.

5. An assembly according to claim 4 wherein the cross-sectional area of the stimulus generator unit is larger than the cross-section area of the detector unit.

6. An assembly according to claim 4 wherein the means for directing contains a duct extending generally normal to the plane of the surface.

7. A hazard detector assembly for attachment to a surface within a protected zone comprising a detector unit, a test stimulus generator unit for generating a stimulus for testing the detector unit and a base unit arranged to be attached to a surface of the detector unit, the stimulus generator unit comprising a body receiving a source of stimulus material and a generator device for generating a stimulus from the source of the stimulus material, the body attached to said base unit and including means for directing the generated stimulus from outside the detector unit towards the detector unit when attached, wherein the body of the stimulus generator unit further comprises means for fixedly mounting the stimulus generator unit to said surface within said protected zone and the stimulus generator unit is adapted to generate a stimulus for testing the detector unit while being fixed to said surface within said protected zone.

8. A hazard detector assembly for attachment to a surface within a protected zone comprising a detector unit, a test stimulus generator unit for generating a stimulus for testing the detector unit and a base unit, wherein the test stimulus generator unit is disposed between the base unit and the detector unit and is connected to the base unit, the base unit being attached to the surface within the protected zone and wherein electrical connections are provided to the base, the stimulus generator unit comprising a body receiving a source of stimulus material, and a generator device for generating a stimulus from the source of the stimulus material, the body being provided with means for attaching to said detector unit to be tested and means for fixedly mounting the stimulus generator to said base unit, the body further comprising means for directing the generated stimulus from outside the detector unit towards the detector unit when attached, the stimulus generator unit being adapted to generate a stimulus for testing the detector unit while being fixed to the base unit.

* * * * *